(12) United States Patent
Moingeon et al.

(10) Patent No.: US 8,632,993 B2
(45) Date of Patent: Jan. 21, 2014

(54) METHOD FOR GRASS SPECIES IDENTIFICATION

(75) Inventors: Philippe Moingeon, Verrieres le Buisson (FR); Thierry Batard, Versailles (FR); Emmanuel Nony, Antony (FR)

(73) Assignee: Stallergenes S.A., Antony Cedex (FR)

( * ) Notice: Subject to any disclaimer, the term of this patent is extended or adjusted under 35 U.S.C. 154(b) by 0 days.

(21) Appl. No.: 13/318,213

(22) PCT Filed: Apr. 30, 2010

(86) PCT No.: PCT/EP2010/055915
§ 371 (c)(1),
(2), (4) Date: Jan. 17, 2012

(87) PCT Pub. No.: WO2010/125186
PCT Pub. Date: Nov. 4, 2010

(65) Prior Publication Data
US 2012/0171710 A1 Jul. 5, 2012

(30) Foreign Application Priority Data
Apr. 30, 2009 (EP) .................................. 09305385

(51) Int. Cl.
*C12Q 1/37* (2006.01)
*C12P 21/06* (2006.01)
(52) U.S. Cl.
USPC .......................................... 435/23; 435/68.1
(58) Field of Classification Search
None
See application file for complete search history.

(56) References Cited

U.S. PATENT DOCUMENTS

| 5,480,972 | A | * | 1/1996 | Avjioglu et al. ............... 530/379 |
| 5,710,126 | A |   | 1/1998 | Griffith et al. |
| 7,112,333 | B1 |  | 9/2006 | Griffith et al. |
| 2009/0197345 | A1 | | 8/2009 | Seppala |

FOREIGN PATENT DOCUMENTS

| WO | WO 94/21675 | * | 9/1994 |
| WO | WO 2007/031080 A1 | * | 3/2007 |

OTHER PUBLICATIONS

Esch, R.E., Methods: A Companion to Methods in Enzymology 13:2-13, 1997.*
International Search Report for PCT/EP2010/055915.
Esch R E; Klapper D G: "Isolation and characterization of a major cross-reactive grass group I allergenic determinant" Molecular Immunology, Pergamon, GB, vol. 26, No. 6, (Jun. 1, 1989), pp. 557-561.
Moingeon P; Peltre G; Bergmann,K -C:"Rationale for a five-grass pollen vaccine" Clinical and Experimental Allergy Reviews, vol. 8, No. 1, (May 2008), pp. 12-14.
Focke M; Marth K; Flicker S; Valenta R: "Heterogeneity of commercial timothy grass pollen extracts" Clinical and Experimental Allergy, vol. 38, No. 8, (Aug. 2008), pp. 1400-1408.
Fenaille Francois; Nony Emmanuel; Chabre Henri; Lautrette Aurelie; Couret Marie-Noelle; Batard Thierry; Moingeon Philippe; Ezan ER: Mass spectrometric investigation of molecular variability of grass pollen group 1 allergens. Journal of Proteome Research Aug. 2009, vol. 8, No. 8, pp. 4014-4027.

* cited by examiner

*Primary Examiner* — David J Steadman
(74) *Attorney, Agent, or Firm* — Browdy and Neimark, PLLC (57) ABSTRACT

The present invention relates to the use of at least one peptide comprising or consisting of a sequence selected from the group consisting of SEQ ID NO: 1, SEQ ID NO: 2, SEQ ID NO: 3, SEQ ID NO: 4 and SEQ ID NO: 5, for determining the presence of extracts from at least one grass species in a composition.

4 Claims, 6 Drawing Sheets

METHOD FOR GRASS SPECIES IDENTIFICATION

FIELDS OF THE INVENTION

The present invention relates to a method for determining if an extract from a grass species is present in a composition

BACKGROUND OF THE INVENTION

Type I allergic diseases such as seasonal allergic rhinitis (hayfever), conjunctivitis, allergic asthma and allergic dermatitis represent a major health problem in industrialised countries (Wuthrich et al. (1989) *Int Arch Allergy Appl Immunol* 90:3-10). It is currently estimated that 15-20% of the population in developed countries are afflicted with some form of allergy.

The major outdoor cause of seasonal hay-fever and allergic asthma is airborne grass pollen (Smart et al. (1982) *Clin Allergy* 12(1):83-9). The most important sources of grass pollen are common agricultural pasture grasses which have been widely introduced throughout the world. For example, in cool temperate regions, grasses such as Rye-grass, Kentucky bluegrass and Timothy (all belonging to the subfamily Pooideae) are of clinical significance.

Antigen-specific tolerance may be defined as the absence or a reduction in intensity, of one or several immune responses, particularly the responses which are responsible for the detrimental action on the organism, to a specific antigen, in the setting of an otherwise normal immune system.

In order to induce antigen-specific tolerance, therapeutic interventions can involve injection or mucosal administration (e.g. oral administration) of the allergen or of mixture of allergens assumed to be responsible for the allergic disorders. With respect to mucosal administration, the sublingual route, for instance, has been explored for antigen administration in a variety of conditions (see e.g. Bahceciler et al. (2005) *Int. Arch. Allergy Immunol.* 136:287-294). In case of grass allergy, sublingual grass tablets can be manufactured using one or several extracts made from pollens obtained from grass species. Examples of such tablets are presently sold under the name Grazax® (*Phleum pratense* pollen extract) by the ALK Abello Company and Oralair® (mixture of pollen extracts from five grass species) by Stallergènes.

Accordingly, there is a need, in particular from quality control organisms or drug agencies, for methods enabling the determination of specific grass allergens in compositions.

Methods known in the art, such as Enzyme-linked immunosorbent assay, are usually time consuming, depend on the availability of specific antibodies and often show a low accuracy. It is therefore an object of the invention to provide an alternative method with improved specificity and accuracy

SUMMARY OF THE INVENTION

The present invention arises from the unexpected finding, by the inventors, that peptides derived from pollen allergens could be used in the identification of specific grass extracts present in compositions.

Thus, the present invention relates to the use of at least one peptide comprising or consisting of a sequence selected from the group consisting of SEQ ID NO: 1, SEQ ID NO: 2, SEQ ID NO: 3, SEQ ID NO: 4 and SEQ ID NO: 5, for determining the presence of extracts from at least one grass species in a composition.

The present invention also relates to a method for determining the presence of extracts from a grass species in a composition, comprising:
  detecting at least one peptide comprising or consisting of a sequence selected from the group consisting of SEQ ID NO: 1, SEQ ID NO: 2, SEQ ID NO: 3, SEQ ID NO: 4 and SEQ ID NO: 5, in a sample of the composition;
  deducing that an extract from Perennial rye, Timothy, Orchard, Sweet vernal, or Kentucky bluegrass is present in the composition, if a peptide comprising or consisting of respectively SEQ ID NO: 1, SEQ ID NO: 2, SEQ ID NO: 3, SEQ ID NO: 4 or SEQ ID NO: 5 has been detected in the sample.

The present invention also relates to peptide comprising a sequence selected from the group consisting of SEQ ID NO: 1, SEQ ID NO: 2, SEQ ID NO: 3, SEQ ID NO: 4 or SEQ ID NO: 5.

The present invention also relates to a kit for detecting the presence of extracts from a grass species in a composition comprising at least two of the peptides according to the invention.

In a preferred embodiment, the kit according to the invention comprises:
  a peptide consisting of SEQ ID NO: 1;
  a peptide consisting of SEQ ID NO: 2;
  a peptide consisting of SEQ ID NO: 3;
  a peptide consisting of SEQ ID NO: 4;
  a peptide consisting of SEQ ID NO: 5.

DETAILED DESCRIPTION OF THE INVENTION

As used herein the term "peptide" denotes a molecule comprising a linear array of D- or L-amino acid residues connected to each other in the linear array by peptide bond. As used herein the "amino acid" notably to include the 20 naturally occurring amino acids (i.e. alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine) but also amino acids harbouring the post-translational modifications which can be found in vivo such as hydroxyproline, phosphoserine and phosphothreonine; and other unusual amino acids including, but not limited to, 2-aminoadipic acid, hydroxylysine, isodesmosine, nor-valine, nor-leucine and ornithine.

Preferably, where the peptide of the invention comprises a sequence selected from SEQ ID NO: 1, SEQ ID NO: 2, SEQ ID NO: 3, SEQ ID NO: 4 or SEQ ID NO: 5, it is less than 100 amino acids long, more preferably less than 70 amino acids long and most preferably it contains no more than 50 amino acids.

More preferably, the peptides of the invention consist in a sequence selected from the group consisting of SEQ ID NO: 1, SEQ ID NO: 2, SEQ ID NO: 3, SEQ ID NO: 4 and SEQ ID NO: 5.

SEQ ID NO: 1, SEQ ID NO: 2, SEQ ID NO: 3, SEQ ID NO: 4 and SEQ ID NO: 5 are respectively fragments of the group 1 allergens Lol p 1 (Perennial rye), Phl p1 (Timothy), Dac g 1 (Orchard), Ant o 1 (Sweet vernal) and Poa p 1 (Kentucky bluegrass).

As intended herein the term "grass" is used to design all monocotyledonous green plants. Preferably, the term "grass species" as used herein refers to species of the Poaceae family (or Gramineae family). More preferably, the term "grass species" refers to species selected in the group consisting of Perennial rye (*Lolium perenne*), Timothy (*Pleum pratense*), Orchard (*Dactylis glomerata*), Sweet vernal (*Anthoxanthum odoratum*), and Kentucky bluegrass (*Poa pratensis*).

As used herein, the term "composition" refers to any mixture likely to contain at least an extract of one grass species, in particular of a grass species selected from the group consisting of Perennial rye, Timothy, Orchard, Sweet vernal, or Kentucky bluegrass.

As used herein the term "extract" refers to a substance made by extracting a part of a raw material. In particular the extract is a pollen extract more particularly a grass pollen extract. The extract is preferably such that it contains allergen proteins, such as Lol p 1, Phl p1, Dac g 1, Ant o 1 and Poa p 1. Preferably, the extract can be obtained after aqueous extraction of grass pollen with an ammonium bicarbonate solution, in particular at a concentration of 4 g/l.

Preferentially, the composition of the invention is a pharmaceutical composition. As used herein the expression "pharmaceutical composition" refers to a composition which is intended to be used for the treatment of a disease. In a preferred embodiment, the pharmaceutical composition is intended to be used in the treatment of allergy, in particular in the treatment of grass allergy. The pharmaceutical composition can be formulated for any administration route, such as the topical, oral, parenteral, intranasal, intravenous, intramuscular, subcutaneous, intraocular or sublingual route. However it is preferred that, the pharmaceutical composition is intended to be administered sublingually.

The peptide of the invention can be detected by any suitable method known in the art. Preferably, detection of the peptide is carried out by a combination of liquid chromatography and mass spectrometry.

As intended herein the expression "liquid chromatography" refers to a technique for the separation of mixture. It usually involves passing a mixture dissolved in a liquid mobile phase through a stationary phase, which separates the analyte to be measured from other molecules in the mixtures and allows it to be isolated. During HPLC, the sample is forced through a column that is packed with irregularly or spherically shaped particles or a porous monolithic layer (stationary phase) by a liquid (mobile phase) at high pressure.

Mass spectrometry is well known to one of skill in the art. Mass spectrometry techniques within the scope of the invention notably encompass MALDI-TOF (matrix assisted laser desorption/ionization-time of flight), or LC-ESI-MS/MS (Liquid chromatography-Electrospray Ionisation-Mass Spectrometry/Mass spectrometry).

The expression "a combination of liquid chromatography and mass spectrometry" is an analytical chemistry technique that combines the physical separation capabilities of liquid chromatography with the mass analysis capabilities of one or several mass spectrometers, preferably after electrospray ionization (ESI), such as tandem mass spectrometry (MS/MS).

Preferably in the above-defined method or use, the extract undergoes proteolytic treatment prior to detecting the peptide. As intended herein, "proteolytic treatment" refers to the directed degradation (digestion) of peptide by enzymes called proteases or intramolecular digestion. Preferably the proteolytic treatment involves at least one protease. Examples of proteases included for example, trypsin, chymotrypsin, elastase, endoproteinase Glu-C, endoproteinase Asp-N, endoproteinase Lys-C, and endoproteinase Pro-C. More preferably, the protease is trypsin. Trypsin is a serine protease which predominantly cleaves peptide chains at the carboxyl side of the amino acids lysine and arginine, except when either is followed by proline.

Preferably, the peptides contain in the kit of the invention are intended to be used as control when a method for determining the presence of extracts from a grass species in a composition is performed.

EXAMPLE

Methods

Pollen Extracts and 5-Grass Pollen Drug Substances

Pollens from Kentucky bluegrass, Orchard, Perennial rye, Sweet vernal and Timothy are individually extracted for 24 hours with an 4 g/L ammonium bicarbonate solution under stirring. The extract is further filtrated, concentrated and lyophilized.

In a second step, to confirm the specificity of markers identified for each grass, extract form mixes containing only 4 of the above grass pollens are also prepared.

Mass Spectrometry (MS) Analyses

In order to confirm the identification of grass specific peptides, drug substances based on mixes containing 4 grass species are characterized by mass spectrometry (MS) techniques in terms of peptide patterns obtained after tryptic digestion. Experimental conditions are initially optimized in order to guarantee the effectiveness of trypsin digestion.

Figure 1:
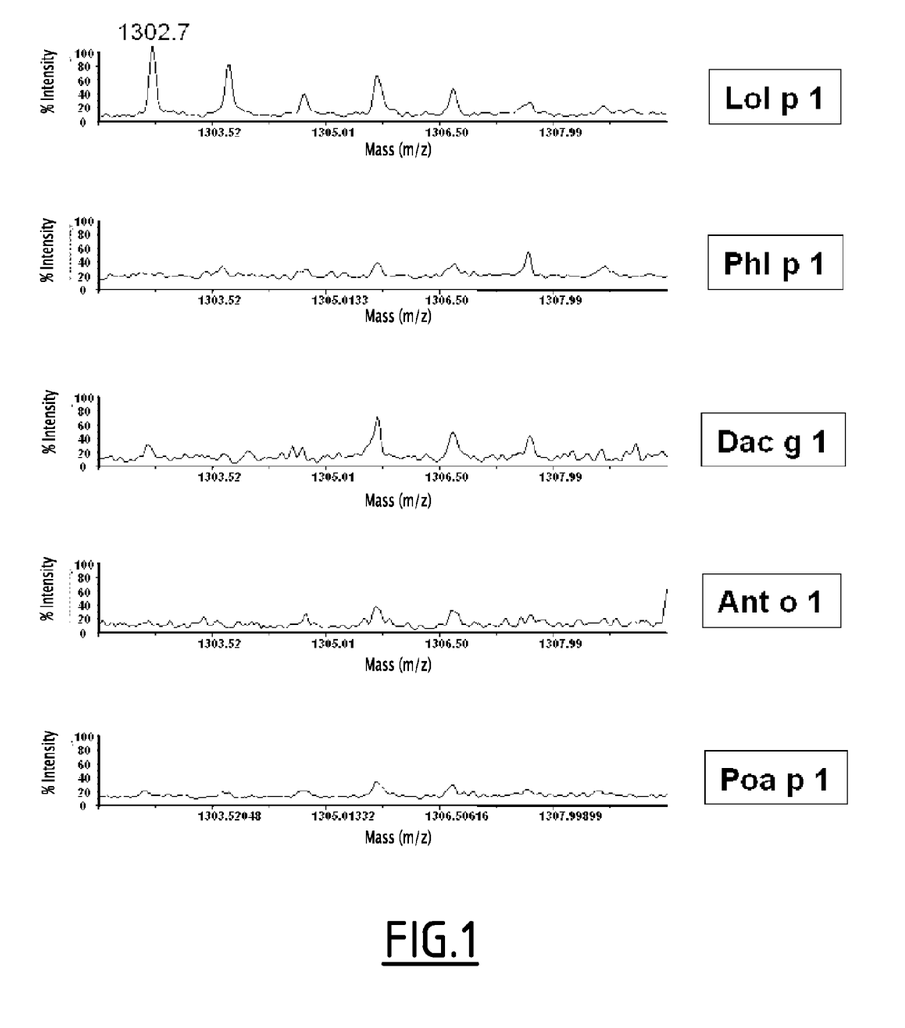
FIG. 1: depicts the MALDI-TOF (matrix assisted laser desorption/ionization-time of flight) spectra purified group 1 allergens Lol p 1, Phl p 1, Dac g 1, Ant o 1, Poa p 1 extract respectively from Perennial rye, Timothy, Orchard, Sweet vernal and Kentucky bluegrass.
Figure 2:
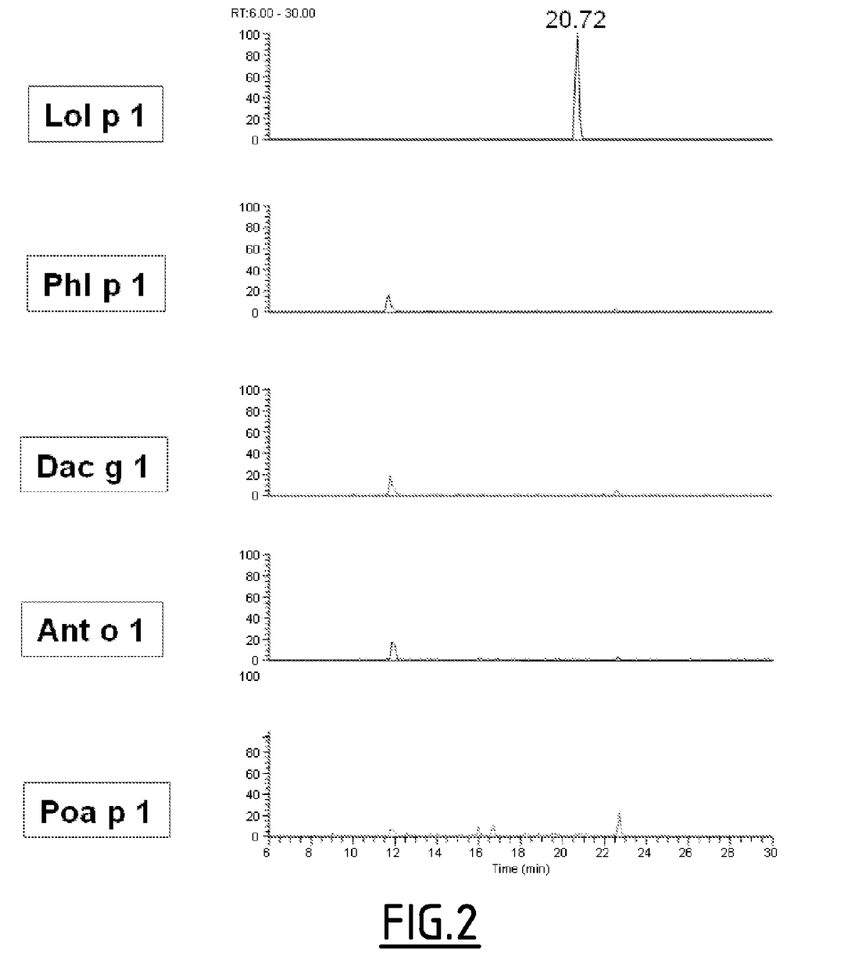
FIG. 2: depicts the ESI-MS (Electrospray Ionisation-Mass Spectrometry) signals corresponding to a peptide at 1302.7 Da from purified group 1 allergens Lol p 1, Phl p 1, Dac g 1, Ant o 1, Poa p 1 extract respectively from Perennial rye, Timothy, Orchard, Sweet vernal and Kentucky bluegrass. Peaks are labelled with retention times in minutes.

Briefly, an aliquot of each purified grass allergen or of purified mix of allergens (~5 µg) is thermally denatured in the presence of an anionic surfactant (Rapigest from Waters Corp). Disulfide bonds are then cleaved after incubation with dithiothreitol and the resulting cysteine residues further alkylated with iodoacetamide, prior to an overnight trypsin digestion. Tryptic digests obtained from the various allergens are then analyzed both by MALDI-TOF MS and LC-ESI-MS/MS for primary structure characterization (FIG. 1 and FIG. 2).

For LC-ESI-MS/MS, 20 μL of an allergen solution (20 μg/mL) are injected on a column for liquid chromatography, such as hydrophobic chromatography, RP— HPLC (Reversed Phase High Pressure Liquid Chromatography), ion-exchange chromatography, size exclusion chromatography and affinity chromatography connected to a Dionex U3000 HPLC. A Q-TOF 1 (Waters) mass spectrometer is connected to the HPLC for accurate mass measurement. This instrument is operated in a positive ionisation mode. The calibration of the instrument is performed using apomyoglobin.

Results

Identification of Species-Specific Group 1 Allergen Peptides

Figure 3:
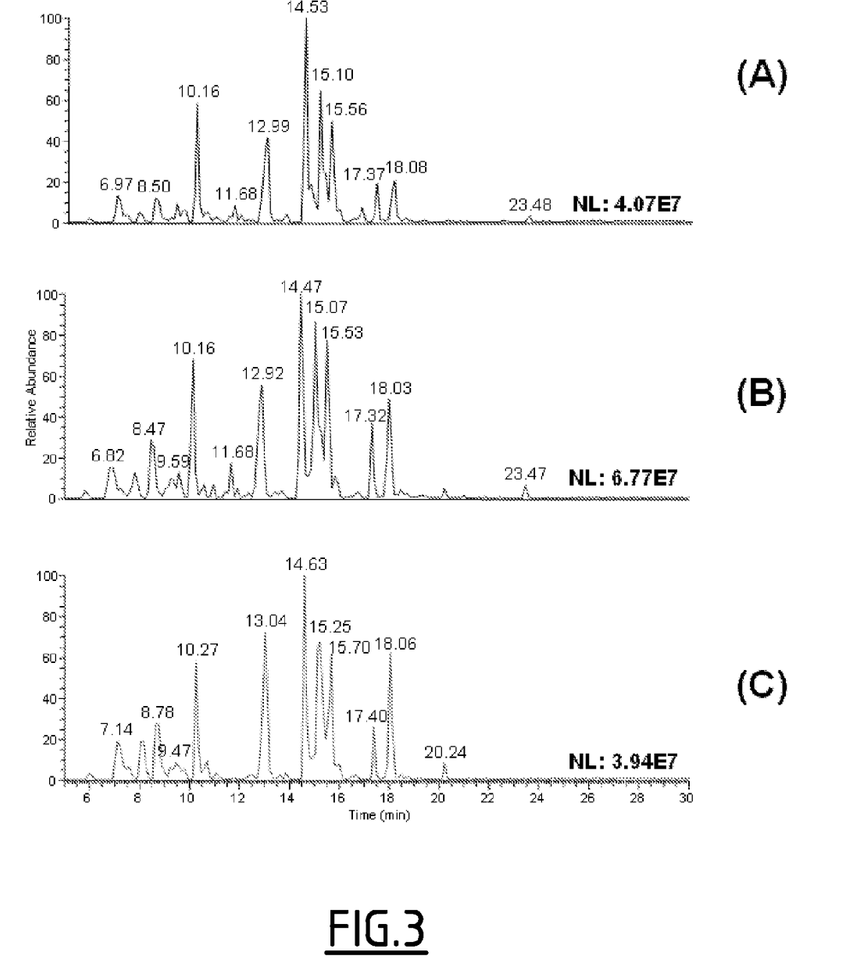
FIG. 3: depicts the full LC-MS (Liquid Chromatography-Mass spectrometry) spectra from the raw extracts of three different batches (A), (B) and (C) of Perennial rye pollen. Peaks are labelled with retention times in minutes.
Figure 4:
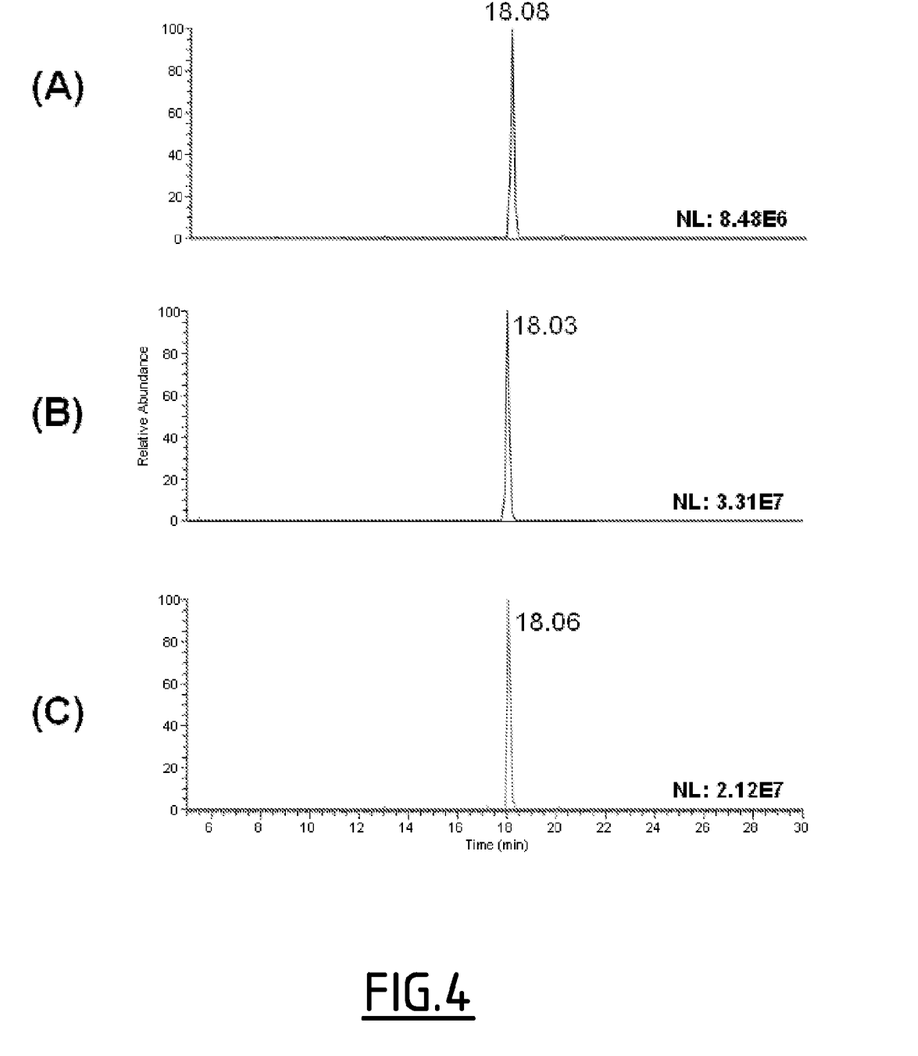
FIG. 4: depicts the LC-MS signal corresponding to peptides from a Lol p 1 extract of Perennial rye pollen with a mass of 1302.7 Da peptides from three different batches (A), (B) and (C). Peaks are labelled with retention times in minutes.

Three independent batches of pollen extracts were analyzed for each grass species to confirm the specificity of those peptides (as exemplified in FIG. 3 and FIG. 4 for *Perennial rye*).

Using a similar approach, a specific tryptic group 1 allergen peptide was successfully identified (with a distinct molecular mass and amino acid sequence) from each individual grass species (Table 1).

TABLE 1

Summary of identified grass species specific markers.

| Allergens Grass species | Molecular mass (Da) | Specific marker amino acid sequence | SEQ ID NO: |
|---|---|---|---|
| Lol p 1 Perennial rye | 1302.7 | ASNPNYLAILVK | 1 |
| Phl p 1 Timothy | 1363.7 | STWYGKPTAAGPK | 2 |
| Dac g 1 Orchard | 4505.0 | CTKPESCSGEAVTVHITDDNE EPIAPYHFDLSGHAFGSMAK | 3 |
| Ant o 1 Sweet vernal | 1499.8 | KVEAEDVIPEGWK | 4 |
| Poa p 1 Kentucky bluegrass | 846.5 | SAGELELK | 5 |

Similarly, three independent batches of pollen extracts were analyzed for each grass species to confirm the specificity of those peptides.

Altogether, these analyses established that mass spectrometry could be used to identify specific group 1 peptides, with precise mass and sequence characteristics, representing molecular signatures for each individual grass species.

Identification of Individual Grasses in 5-Grass Pollen Extracts

Having identified species-specific group 1 peptides for each of the 5 grass species, it was investigated whether such peptides could be detected in 5-grass pollen extracts. At first, grass pollen raw extracts comprising only 4 species were analyzed, to confirm peptide allergen-specificity. An LC-MS/MS approach (using an LTQ-Orbitrap mass spectrometer from ThermoElectron) was used to detect species specific group 1 peptides. The presence of all specific peptides could be detected directly by LC-MS/MS in these samples.

Figure 5:
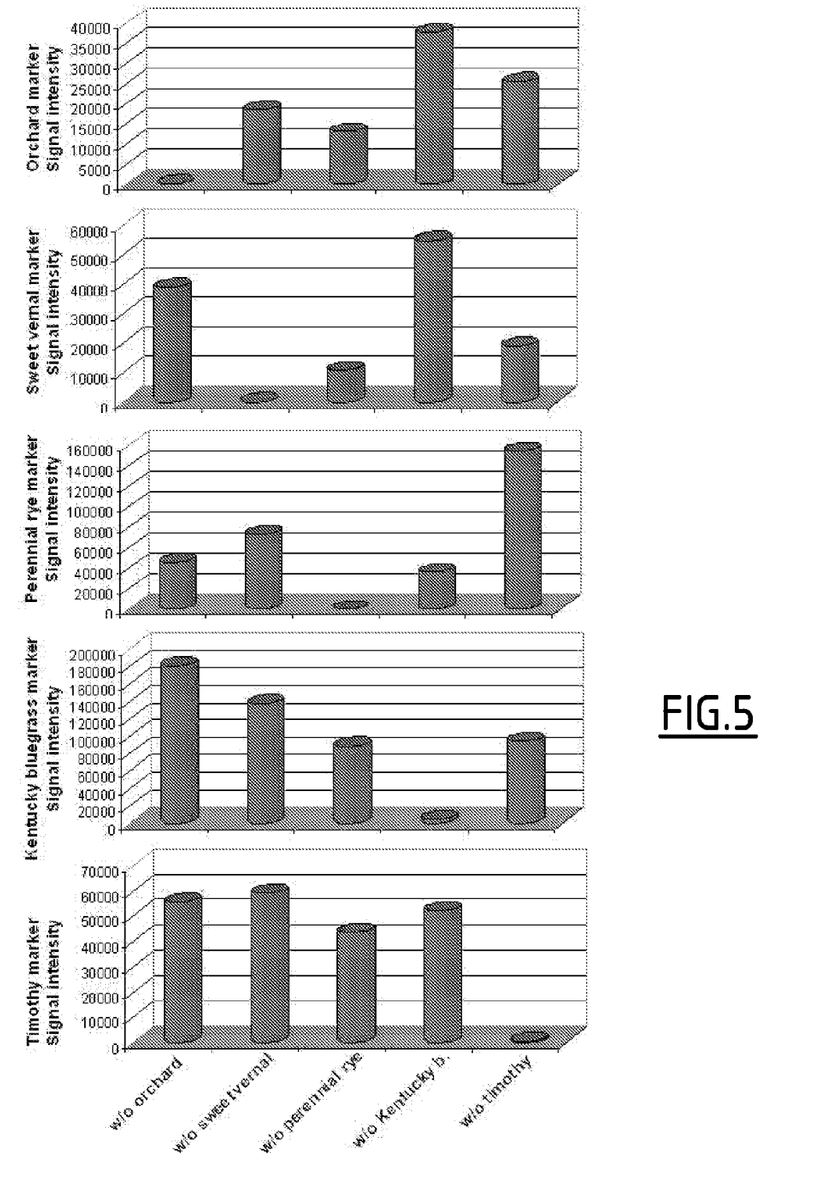
FIG. 5: Depicts the intensity of the detection of Orchard marker, Sweet vernal marker, Perennial rye marker, Kentucky bluegrass marker and Timothy marker (vertically) measured by MS/MS analysis in grass mixture without orchard (w/o orchard), without sweet vernal (w/o sweet vernal), without Perennial rye (w/o perennial rye) without Kentucky bluegrass (w/o Kentucky b.) or without Timothy (w/o Timothy) (horizontally).

As an example, using this method, the 4505.0 Da peptide (Dac g 1 specific peptide) was not detected in an extract made from a 4-grass mix lacking orchard, but was detected in all 4 grass mixes containing orchard (FIG. 5). Individual markers specific for other species were not detected in 4-grass mixes lacking the corresponding grass species (FIG. 5).

Figure 6:
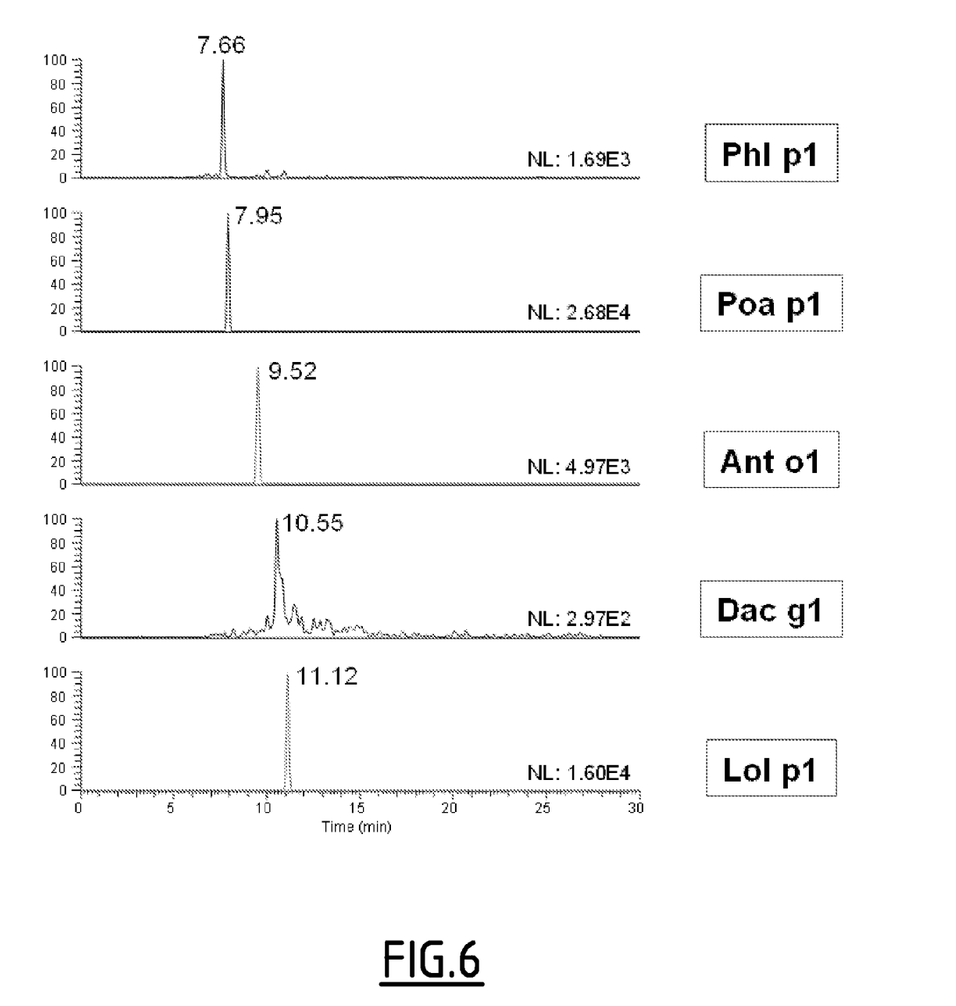
FIG. 6: depicts the detection of specific group 1 peptides signal of Phl p 1, Poa p 1, Ant o 1, Dac g 1, Lol p 1 in a 5-grass pollen extract by LC-MS/MS. Peaks are labelled with retention times in minutes.

With this approach, all the five allergen-specific peptides could unambiguously be detected in a drug substance made from a 5-grass pollen mix (FIG. 6). Similar results were obtained with two additional drug substances prepared independently with distinct pollens.

Thus, this study provides a test to identify or to confirm the presence of a grass species within a mixture containing an extract of grass species.

This study also provides a sensitive identity test to document the presence of each individual grass species within drug substances manufactured from 5-grass pollen extracts.

Group 1 allergen-derived peptides were first identified with specific masses and amino acid sequence characteristics, which could be used as molecular signatures for each individual grass species. Using a LC-MS/MS methodology, a high level of detection specificity was reached when combining (i) MS/MS signals, (ii) high resolution mass measurements, and (iii) chromatographic retention times. Thus, it was shown that such group 1-derived peptides are truly specific for individual grass species as confirmed in three different batches for each individual pollen.

The invention claimed is:

1. A method for determining the presence of grass species extracts in a grass pollen extract composition, comprising:
    subjecting a sample of grass pollen extract to proteolytic treatment that cleaves peptide chains at the carboxyl side of the amino acids lysine and arginine, except when either is followed by proline, to obtain a mixture of peptides;
    subjecting the mixture of peptides to an analytical chemistry technique to specifically determine the presence of peptides, within the mixture of peptides, that consist of the amino acid sequences of SEQ ID NO: 1, SEQ ID NO: 2, SEQ ID NO: 3, SEQ ID NO: 4 and SEQ ID NO: 5;
    determining the presence of pollen from each of Perennial rye, Timothy, Orchard, Sweet vernal, and Kentucky bluegrass if a peptide consisting of the amino acid sequence of SEQ ID NO: 1, SEQ ID NO: 2, SEQ ID NO: 3, SEQ ID NO: 4 or SEQ ID NO: 5, respectively, is detected in the sample.

2. The method according to claim 1, wherein the analytical chemistry technique is a combination of liquid chromatography and mass spectrometry.

3. The method according to claim 1, wherein the proteolytic treatment is with trypsin.

4. The method according to claim 1, wherein the presence of peptides, within the mixture of peptides, that consist of the amino acid sequences of SEQ ID NO: 1, SEQ ID NO: 2, SEQ ID NO: 3, SEQ ID NO: 4 and SEQ ID NO: 5 is determined using peptides consisting of the amino acid sequences of SEQ ID NO: 1, SEQ ID NO: 2, SEQ ID NO: 3, SEQ ID NO: 4 and SEQ ID NO: 5 as controls.

* * * * *

SEQUENCE LISTING

```
<160> NUMBER OF SEQ ID NOS: 5

<210> SEQ ID NO 1
<211> LENGTH: 12
<212> TYPE: PRT
<213> ORGANISM: artificial sequence
<220> FEATURE:
<223> OTHER INFORMATION: a derived polypeptide sequence based on a
      corresponding polypeptide sequence in a target grass species

<400> SEQUENCE: 1

Ala Ser Asn Pro Asn Tyr Leu Ala Ile Leu Val Lys
1               5                   10

<210> SEQ ID NO 2
<211> LENGTH: 13
```

-continued

```
<212> TYPE: PRT
<213> ORGANISM: artificial sequence
<220> FEATURE:
<223> OTHER INFORMATION: a derived polypeptide sequence based on a
      corresponding polypeptide sequence in a target grass species

<400> SEQUENCE: 2

Ser Thr Trp Tyr Gly Lys Pro Thr Ala Ala Gly Pro Lys

<210> SEQ ID NO 3
<211> LENGTH: 41
<212> TYPE: PRT
<213> ORGANISM: artificial sequence
<220> FEATURE:
<223> OTHER INFORMATION: a derived polypeptide sequence based on a
      corresponding polypeptide sequence in a target grass species

<400> SEQUENCE: 3

Cys Thr Lys Pro Glu Ser Cys Ser Gly Glu Ala Val Thr Val His Ile
1               5                   10                  15

Thr Asp Asp Asn Glu Glu Pro Ile Ala Pro Tyr His Phe Asp Leu Ser
            20                  25                  30

Gly His Ala Phe Gly Ser Met Ala Lys
        35                  40

<210> SEQ ID NO 4
<211> LENGTH: 13
<212> TYPE: PRT
<213> ORGANISM: artificial sequence
<220> FEATURE:
<223> OTHER INFORMATION: a derived polypeptide sequence based on a
      corresponding polypeptide sequence in a target grass species

<400> SEQUENCE: 4

Lys Val Glu Ala Glu Asp Val Ile Pro Glu Gly Trp Lys
1               5                   10

<210> SEQ ID NO 5
<211> LENGTH: 8
<212> TYPE: PRT
<213> ORGANISM: artificial sequence
<220> FEATURE:
<223> OTHER INFORMATION: a derived polypeptide sequence based on a
      corresponding polypeptide sequence in a target grass specieseptide

<400> SEQUENCE: 5

Ser Ala Gly Glu Leu Glu Leu Lys
1               5
```